United States Patent [19]
Evanoski, III

[11] 4,367,740
[45] Jan. 11, 1983

[54] COMBINATION CATHETER CYSTOMETER SYSTEM AND GASTRIC FEEDING DEVICE

[76] Inventor: Constant J. Evanoski, III, 868 36th St., Altoona, Pa. 16601

[21] Appl. No.: 214,640

[22] Filed: Dec. 10, 1980

[51] Int. Cl.³ .......................................... A61M 25/00
[52] U.S. Cl. .................... 604/43; 128/748; 604/102; 604/100; 604/103
[58] Field of Search .......... 128/748, 348, 349, 350 R, 128/340 V, 349 B, 349 BV, 240, 241, 246, 344

[56] References Cited

U.S. PATENT DOCUMENTS

| | | | |
|---|---|---|---|
| 2,286,462 | 6/1942 | Chaffin | 128/350 R |
| 2,898,917 | 8/1959 | Wallace | 128/350 R |
| 3,429,314 | 2/1969 | Ericson | 128/349 R |
| 3,513,849 | 5/1970 | Vaillancourt et al. | 128/350 R |
| 3,583,404 | 6/1971 | McWhorter | 128/349 BV |
| 3,726,281 | 4/1973 | Norton et al. | 128/349 R |
| 4,016,879 | 4/1977 | Mellor | 128/214.4 |
| 4,217,911 | 8/1980 | Layton | 128/748 |

*Primary Examiner*—Dalton L. Truluck
*Attorney, Agent, or Firm*—Harpman & Harpman

[57] ABSTRACT

A catheter related cystometer system and gastric feeding device is usable as a urinary catheter providing a sealed drainage tube with a normally closed access opening for injecting an irrigating liquid into the drainage tube and the bladder in which the catheter is positioned. An adaptation of the device enables it to be used as a cystometry system to measure the pressure volume relationship in the bladder of a patient from a source of fluid and further adaptation enables the device to be used as a gastric feeding device by being placed in a desired location in a patient and communication established with an IV bottle or the like.

3 Claims, 7 Drawing Figures

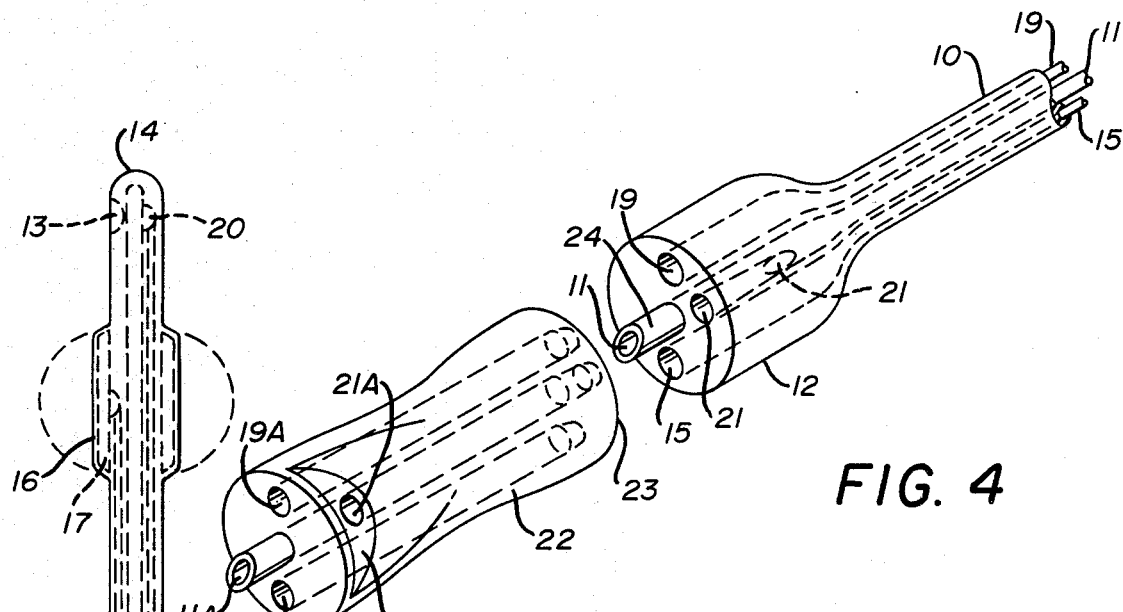
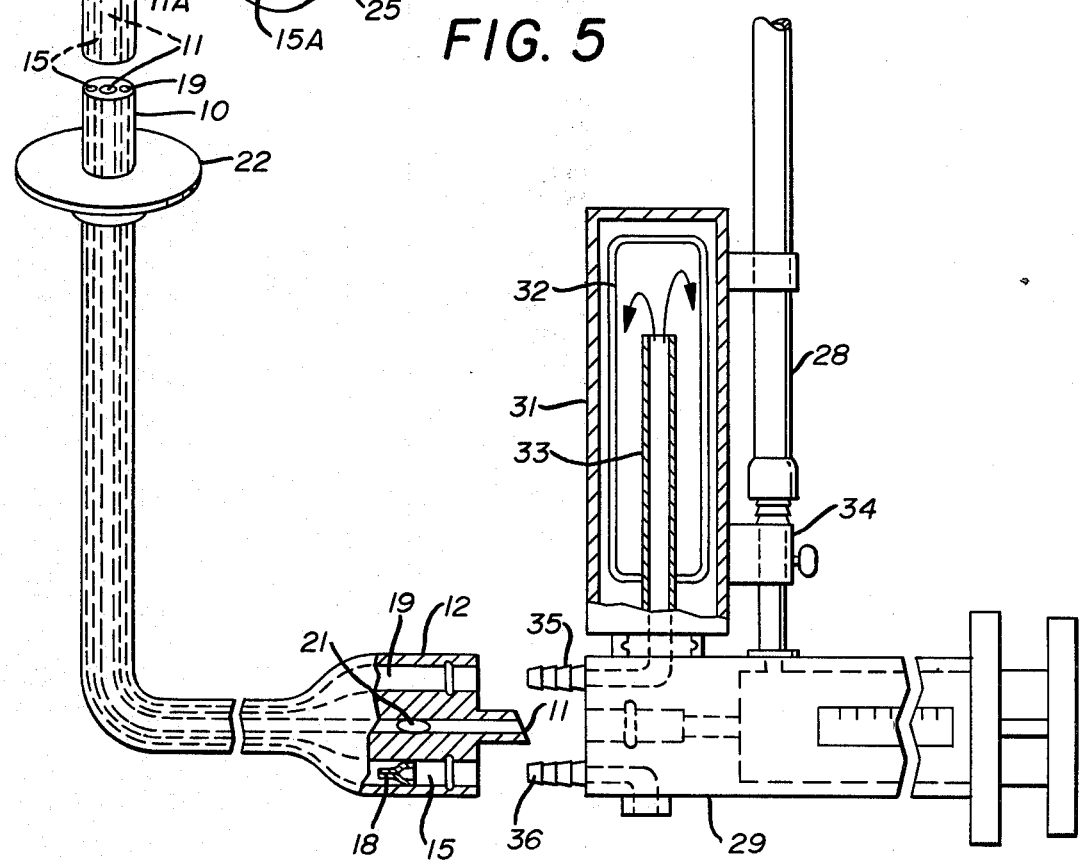
FIG. 4
FIG. 5
FIG. 1
FIG. 2

4,367,740

COMBINATION CATHETER CYSTOMETER SYSTEM AND GASTRIC FEEDING DEVICE

BACKGROUND OF THE INVENTION

1. Field of the Invention

The present invention relates to a combination catheter cystometer system and gastric feeding device.

2. Description of the Prior Art

Urinary catheters have been generally used for draining of fluids from a body cavity by gravitational means and such catheters are disclosed in U.S. Pat. Nos. 3,429,314, 3,726,281 and 4,217,911. An irrigation adaptor for use with a catheter is disclosed in U.S. Pat. No. 3,800,799.

The catheters of the above cited patents are generally similar in that they each provide separate lumens, one of which is the main drainage lumen, another of which is used for the inflation of the customary balloon and a lubrication lumen is added in U.S. Pat. No. 3,726,281.

The prior art patents fail to provide a sealed or closed drainage system as desirable in controlling infection in a patient in which a catheter is used. The irrigation adaptor of U.S. Pat. No. 3,800,799 permits irrigation liquid to be introduced into a catheter drainage lumen, but requires the installation of the adaptor in either the drain or the connection between the drain and the catheter and as such provides access for bacteria into the system.

The present invention provides essentially a modified and improved catheter having a main drainage lumen, a normally closed access opening in communication therewith into which a sterile irrigating fluid may be introduced while the system remains closed and by utilizing adaptors as disclosed enables the implanted catheter to be used as an essential part of a cystometry system.

The device disclosed herein has the further advantage in that it can be readily adapted for gastric feeding by surgical implantation and attachment in a patient establishing the desired communicating or feeding path.

SUMMARY OF THE INVENTION

A combination catheter, cystometry system and gastric feeding device provides a flexible body member having a discharge lumen communicating with an infusion opening adjacent a distal end of the device and an inflation lumen communicating with a balloon adjacent the distal end of the device and an irrigation lumen communicating with the drainage lumen adjacent the distal end of the device. A separate and distinct access opening communicates with the drainage lumen to provide a passageway in which sterile irrigating fluids may be introduced into the body cavity through the main drainage lumen. The proximal end of the catheter portion of the device provides for the adaptation of the catheter to permit its use as a cystometer system or alternately as a gastric feeding device.

DESCRIPTION OF THE DRAWINGS

FIG. 1 is a side elevational view with parts broken away and parts in cross section with broken lines illustrating the several lumens extending axially of the device;

FIG. 2 is a side elevational view of an adaptor for use with the catheter of FIG. 1 and incorporating a gastric feeding bottle to prevent dumping syndrome;

FIG. 4 is a perspective elevation of the proximal end of the catheter illustrated in FIG. 1 of the drawings;

FIG. 5 is a perspective view of a first adaptor attachable to the proximal end of the catheter seen in FIGS. 1 and 4 of the drawings;

DESCRIPTION OF THE PREFERRED EMBODIMENTS

Figure 3:
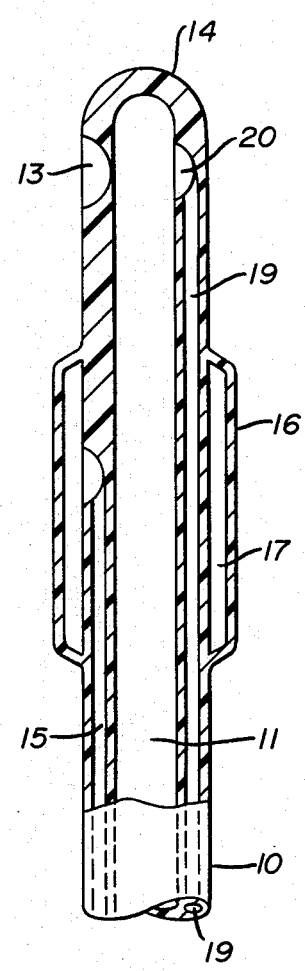
FIG. 3 is an enlarged cross sectional elevation of the distal end of the catheter seen in FIG. 1 of the drawings.

Referring now to FIGS. 1, 2 and 3 of the drawings, there is shown a catheter having an elongated flexible shaft 10 defining a drainage lumen 11 extending from the proximal end 12 of the catheter to an opening 13 adjacent a distal end 14 of the catheter, a pressure lumen 15 extending from the proximal end 12 to an inflatable balloon 16 of elastic material having opposed ends secured in circumferential zones to an outer surface of the catheter shaft 10. The balloon 16 defines a cavity 17 which may be inflated through the pressure lumen 15. A valve 18 is located in the pressure lumen 15 in the proximal end 12 of the catheter so that inflation fluid introduced into the balloon cavity 17 may be retained therein as desired.

The flexible shaft 10 of the catheter also defines an irrigating lumen 19 which extends from the proximal end 12 of the catheter to an opening 20 which communicates with the drainage lumen 11 adjacent the distal end 14 of the catheter.

An opening 21 is formed in the proximal end 12 of the catheter in communication with the drainage lumen 11 as also illustrated in FIG. 4 of the drawings.

Figure 7:
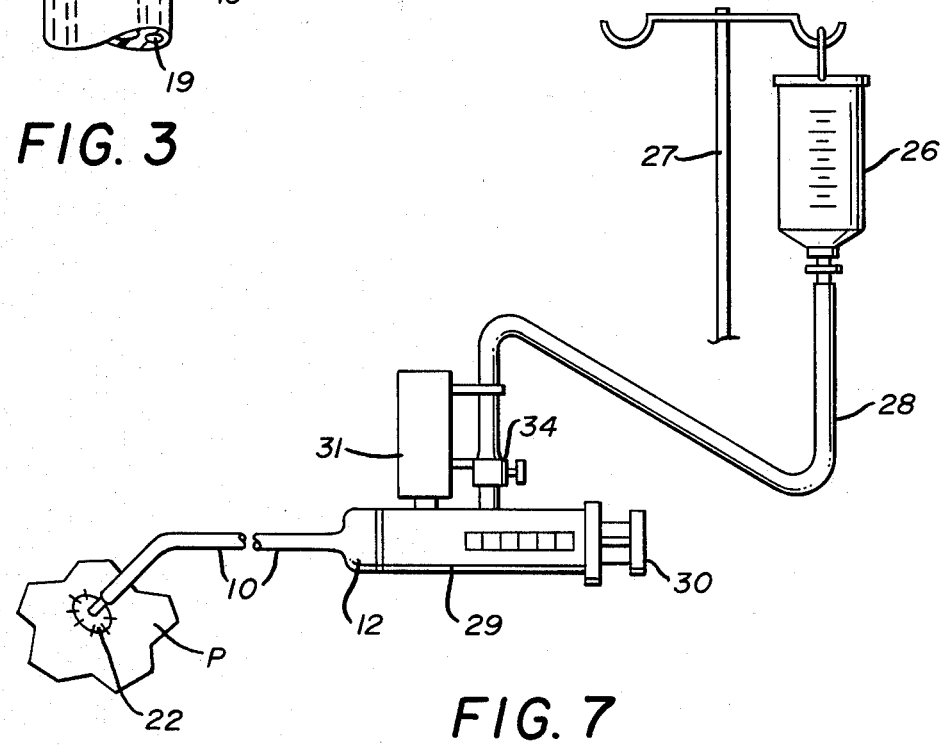
FIG. 7 is a diagrammatic view of a gastric feeding system incorporating the catheter illustrated in FIGS. 1 and 2 of the drawings.

Still referring to FIG. 1 of the drawings, it will be seen that a collar 22 is positioned around and attached to the flexible shaft 10 of the catheter and as illustrated in FIG. 7 of the drawings, the collar 22 is used to secure the catheter in position with respect to the body of a patient P and secured thereto by sutures when the invention disclosed herein is used as a gastric feeding device.

It will occur to those skilled in the art that the construction of the catheter hereinbefore described as including several lumens extending from the proximal end 12 to points adjacent the distal end 14 of the flexible shaft 10, enable the device to act to prevent the development of negative pressure in a patient's bladder or other body cavity as such a negative pressure has been known to form pseudo-polyps in the tissue of the bladder at times to the extent resulting in a hemorrhagic condition.

It will also occur to those skilled in the art that the catheter disclosed herein has certain unique advantages in that once installed, the bladder can be irrigated through the same without destroying the bacterial seal which results from the use of the device and that in the event the drainage lumen 11 clogs as from a clot or the like, as occurs frequently, the same may be removed by introducing suitable sterile fluid under pressure in the lumen 11, without disconnecting the catheter from its receiving bag and without permitting the introduction of bacteria or opening the system. The opening 21 also permits instilling a medication without opening the main connection to the receiving bag.

By referring now to FIG. 5 of the drawings, it will be seen that a first adaptor 22 is arranged to be positioned with an end 23 thereof in engagement with the proximal end 12 of the catheter. The first adaptor 22 is provided with a plurality of lumens therein which establish communication with the lumens 11, 15 and 19 in the catheter and the opening 21 which as previously noted extends inwardly and communicates with the lumen 11. In the first adaptor 22 a central opening in the end 23 receives a tubular extension 24 forming the lumen 11 in the proximal end 12 of the catheter and the first adaptor 22 has three similar formed projecting tubular members arranged for engagement in the openings forming the ends of the lumens 15 and 19 and the opening 21. Passageways extend from the end 23 of the first adaptor 22 to the opposite or left end of the first adaptor 22 as seen in FIG. 5 with the extension of the lumen 11 indicated by the numeral 11A, the extension of the lumen 15 indicated by the numeral 15A, and the extension of the lumen 19 indicated by the numeral 19A. The end of the passageway that communicates with the opening 21 in the proximal end 12 of the catheter is positioned in a shoulder 25 and indicated by the numeral 21A.

The opening 21A is normally plugged so that the communication with the lumen 11 remains sterile, but provides an access opening in which sterile fluid may be introduced to be directed into the bladder or other body cavity in which the catheter is positioned.

By referring now to FIGS. 2 and 7, it will be seen that the catheter of FIG. 1 may be used with a second adaptor to provide a gastric feeding device. As will be understood by those skilled in the art a gastric feeding device is a flexible tubular member positioned into the stomach or adjacent food channels of a patient through an incision in the patient's body as indicated at P in FIG. 7 with the proximal end of the device placed in communication with a source of food such as an IV bottle 26.

In FIG. 7 the IV bottle 26 is shown suspended from a stand 27 and in communication with a tubular member 28 which in turn communicates with a syringe 29. The syringe 29 has a chamber therein in which a piston 30 is reciprocally mounted and the chamber in the syringe 29 also communicates with a bottle in a housing 31 mounted on the side of the syringe 29. The bottle is indicated by the numeral 32 in FIG. 2 of the drawings and it will be seen to be inverted and positioned around a tubular member 33 which forms the actual means of communication with the chamber in the syringe 29. Those skilled in the art will observe that spasms affecting the area with which the gastric feeding tube communicates will temporarily create a backflow in the system which is absorbed in the bottle 32 and held therein inasmuch as the upper end of the tubular member 33 is substantially above the lower end of the bottle 32.

Still referring to FIG. 2 of the drawings, it will be seen that the tubular member 28 communicates with the syringe 29 by way of a valve 34 so that the rate of supply from the IV bottle 26 may be controlled.

The left end of the syringe 29 is provided with projecting tubular members 35 and 36 which will register with the openings in the proximal end 12 of the catheter.

Figure 6:
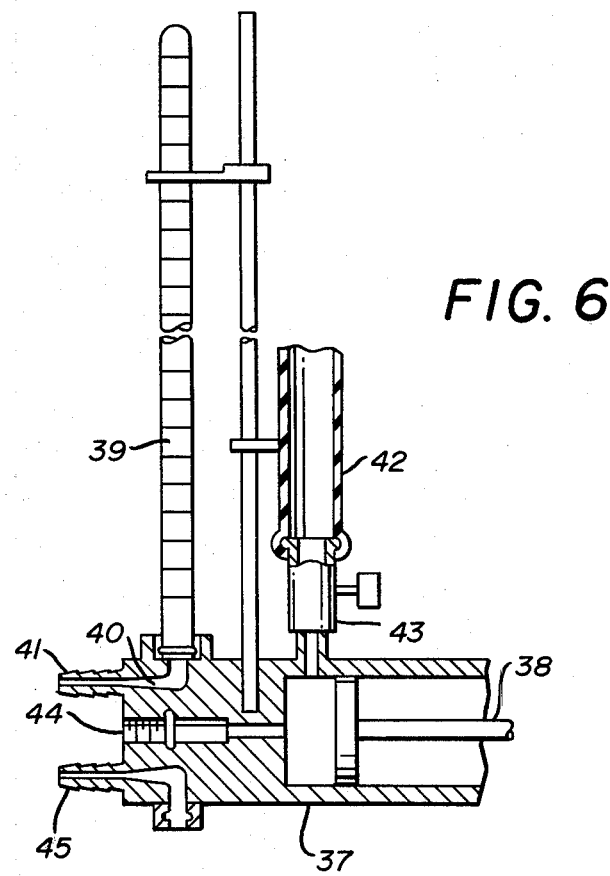
FIG. 6 is a side elevation with parts in cross section and parts broken away illustrating the cystometry system of the present invention.

By referring now to FIG. 6 of the drawings, it will be seen that a third adaptor enables the catheter of FIGS. 1, 3 and 4 of the drawings to be used as a cystometer system comparable with the disclosure of the aforementioned U.S. Pat. No. 4,217,911. In FIG. 6 of the drawings, the adaptor body 37 forms a chamber in which a piston 38 is reciprocally mounted in the manner of a syringe and that the chamber defined by the adaptor body 37 supports a manometer 39 which communicates by way of a passage 40 with a tubular extension 41. A source of liquid communicates with the chamber in the adaptor 37 by way of a flexible tube 42 which is controlled by a valve 43 and the chamber in the adaptor 37 communicates with an axial passageway 44 which will receive the tubular extension defining the drainage lumen 11 as indicated by 11A in the first adaptor 22 heretofore described and illustrated in FIG. 5 of the drawings.

The lumen 15 and its extension through the first adaptor 22 communicates with the tubular extension 45 on the adaptor 37.

Those skilled in the art will observe that the combination of the catheter of FIGS. 1, 3 and 4 of the drawings and the adaptor 37 of FIG. 6 make it possible for a urologist to measure the static pressure-volume relationship in a bladder of a patient in order to determine the capacitance of the bladder as a function of pressure and volume. The procedure includes the infusion of a known volume of fluid such as water or gas into the bladder through the device and measuring the resulting pressure in the bladder on the manometer. In the adaptor 37 the introduction of the desired volume of liquid or gas is followed by the closing of the valve 43 and the stationary positioning of the piston 38 whereupon the correct pressure reading of the pressure in the bladder may be obtained on the manometer 39 by reading the height of the fluid therein.

It will thus be seen that the combination catheter, cystometer system and gastric feeding device disclosed herein has multiple uses and that the essential and common portion of the device regardless of its use comprises the improved catheter with its drainage lumen 11, its pressure lumen 15 and its irrigating lumen 19 and that it is used either directly with the adaptors as seen in FIGS. 6 and 7 or with the first adaptor as seen in FIG. 5 in order to accommodate the various usages of which it is capable.

The foregoing detailed description is given for clearness of understanding only and no unnecessary limitations should be understood therefrom as modifications will be obvious to those skilled in the art. Having thus described my invention what I claim is:

1. An improvement in a catheter adapted for insertion into a body passage of restricted size and also usable in a cystometer system and in a gastric feeding device and comprising an elongated flexible shaft, a drainage lumen defined by said flexible shaft and extending from a first opening adjacent the distal end of the flexible shaft to the proximal end thereof, an inflatable balloon about said flexible shaft inwardly from the distal end thereof, a pressure lumen defined by said flexible shaft and extending from said balloon to the proximal end of said flexible shaft, an irrigating lumen defined by said flexible shaft communicating with said drainage lumen in the distal end of said flexible shaft and extending to the proximal end of said flexible shaft, the improvement comprising means for introducing sterile fluid into said drainage lumen and thereby into said body passage while said catheter is inserted in said body passage, said means including a second opening in said drainage lumen adjacent said proximal end of said flexible shaft, a passageway in said proximal end of said flexible shaft communicating with said second opening and with the exterior of said proximal end of said flexible shaft and removable means normally closing said second opening.

2. The improvement in a catheter set forth in claim 1 and wherein said proximal end of said flexible shaft is cross sectionally circular and wherein said drainage lumen communicates with a tubular extension centered in said cross sectionally circular proximal end and wherein said second opening and said passageway communicate with a fourth opening in said cross sectionally circular proximal end.

3. The improvement in a catheter set forth in claim 1 and wherein said means normally closing said second opening consists of a plug of self-sealing material removably positioned in said second opening.

* * * * *